(12) United States Patent
Athanasiou et al.

(10) Patent No.: US 7,226,450 B2
(45) Date of Patent: *Jun. 5, 2007

(54) TISSUE PENETRATING DEVICE AND METHODS FOR USING SAME

(75) Inventors: Kyriacos A. Athanasiou, San Antonio, TX (US); George Constantinides, San Antonio, TX (US); Dan R. Lanctot, San Antonio, TX (US)

(73) Assignee: The Board of Regents of the University of Texas Systems, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/266,452

(22) Filed: Oct. 8, 2002

(65) Prior Publication Data
US 2003/0114858 A1 Jun. 19, 2003

Related U.S. Application Data

(60) Continuation of application No. 09/757,122, filed on Jan. 9, 2001, now Pat. No. 6,527,778, which is a division of application No. 09/033,105, filed on Mar. 2, 1998, now Pat. No. 6,183,442.

(51) Int. Cl.
*A61B 17/00* (2006.01)
*A61F 5/00* (2006.01)

(52) U.S. Cl. .......................... 606/80; 606/79; 606/86; 604/154; 604/156; 604/198

(58) Field of Classification Search ................ 606/185, 606/79, 80, 86; 604/117, 198, 197, 196, 604/263, 154, 156
See application file for complete search history.

(56) References Cited

U.S. PATENT DOCUMENTS

| 2,317,648 | A |   | 4/1943 | Siqveland |          |
|-----------|---|---|--------|-----------|----------|
| 2,679,843 | A | * | 6/1954 | May       | 604/68   |
| 2,701,566 | A | * | 2/1955 | Krug      | 604/154  |
| 2,904,045 | A | * | 9/1959 | Owings    | 604/274  |
| 4,660,570 | A | * | 4/1987 | Dombrowski| 600/578  |

(Continued)

FOREIGN PATENT DOCUMENTS

FR 2581548 5/1985

(Continued)

OTHER PUBLICATIONS

Waisman, M. et. al., Intraosseous Regional Anesthesia as an Alternative to Intravenous Regional Anesthesia. Journal of Trauma: Injury, Infection, and Critical Care v. 39: pp. 1153-1156, 1995.

(Continued)

*Primary Examiner*—Pedro Philogene
(74) *Attorney, Agent, or Firm*—Robert W Strozier

(57) ABSTRACT

A device for tissue, especially hard tissue, penetration which incorporated a novel paddle-shaped needle for low friction rotatory penetration of the tissue. A controlled delivery or extraction system is also disclosed for the transfer of material from the device into a tissue site or transfer of material from the tissue site to the device. The delivery system or extraction system includes at least on solenoid or other similar device.

24 Claims, 8 Drawing Sheets

U.S. PATENT DOCUMENTS

| | | | |
|---|---|---|---|
| 4,695,274 A * | 9/1987 | Fox | 604/198 |
| 4,787,893 A | 11/1988 | Villette | |
| 4,919,146 A | 4/1990 | Rhinehart et al. | |
| 4,950,246 A * | 8/1990 | Muller | 604/154 |
| 4,969,870 A | 11/1990 | Kramer et al. | |
| 5,122,114 A | 6/1992 | Miller et al. | |
| 5,139,500 A | 8/1992 | Schwartz | |
| 5,178,628 A | 1/1993 | Otsuka et al. | |
| 5,195,985 A | 3/1993 | Hall | |
| 5,263,974 A | 11/1993 | Matsutani et al. | |
| 5,312,364 A | 5/1994 | Jacobs | |
| 5,332,398 A | 7/1994 | Miller et al. | |
| 5,431,655 A | 7/1995 | Melker et al. | |
| 5,476,480 A | 12/1995 | Matsutani et al. | |
| 5,478,328 A | 12/1995 | Silverman et al. | |
| 5,690,618 A * | 11/1997 | Smith et al. | 604/232 |
| 5,762,639 A | 6/1998 | Gibbs | |
| 5,779,708 A | 7/1998 | Wu | |
| 5,810,826 A | 9/1998 | Akerfeldt et al. | |
| 5,848,996 A | 12/1998 | Eldor | |
| 5,927,976 A | 7/1999 | Wu | |
| RE36,447 E * | 12/1999 | Byrne et al. | 604/198 |
| 6,096,042 A | 8/2000 | Herbert | |
| 6,135,769 A | 10/2000 | Kwan | |
| 6,183,442 B1 * | 2/2001 | Athanasiou et al. | 604/154 |
| 6,210,376 B1 | 4/2001 | Grayson | |
| 6,213,977 B1 * | 4/2001 | Hjertman et al. | 604/117 |
| 6,217,561 B1 | 4/2001 | Gibbs | |
| 6,228,088 B1 | 5/2001 | Miller et al. | |
| 6,247,928 B1 | 6/2001 | Meller et al. | |
| 6,273,715 B1 | 8/2001 | Meller et al. | |
| 6,283,970 B1 | 9/2001 | Lubinus | |
| 6,287,114 B1 | 9/2001 | Meller et al. | |
| 6,315,737 B1 | 11/2001 | Skinner | |
| 6,547,755 B1 * | 4/2003 | Lippe et al. | 604/67 |
| 2001/0012926 A1 | 8/2001 | Gross et al. | |
| 2001/0014439 A1 | 8/2001 | Meller et al. | |
| 2001/0053888 A1 | 12/2001 | Athanasiou et al. | |
| 2002/0042581 A1 | 4/2002 | Cervi | |

FOREIGN PATENT DOCUMENTS

| | | |
|---|---|---|
| GB | 1452790 | 10/1976 |
| JP | WO 79/00221 | 5/1979 |
| WO | WO 96/25965 | 2/1995 |

OTHER PUBLICATIONS

Steinbach, Howard L. et al. , Osseous Phlebography. Surgery, Gynecology & Obstetrics, Feb. 1957, pp. 215-226.

Waisman, M. et. al., Bone Marrow Infusion in Adults. Journal of Trauma: Injury, Infection, and Critical Care vol. 42: pp. 288-293, 1997.

Grisham, Jonathan, et. al. Bone Marrow Aspirate as as Accessible and Reliable Source for Critical Laboratory Studies. Annals of Emergency Medicine vol. 20, pp. 1121-1124, Oct. 1991.

Rosetti, Valerie, A. et. al., Intraosseous Infusion: an alternative Route of Pediatric Intravascular Access. Annals of Emergency Medicine vol. 14, pp. 885-888, Sep. 1985.

Grady, Denise. By Giving Her Bone Marrow to A Stranger, an Illinois Mother Went Beyond The Call. Time. Fall 1997. p. 69-70.

Intraosseous Infusion. http://www.life-assist.com/intraosseous. html. p. 1 Baxter Jamshidi Intraosseous Needles. www.life-assit.com/jamshidi.html. p. 2 Intraosseous Infusion Needles. Baxter. www.life-assit.com/jamshidi.html. p. 1.

B. I. G. Bone Injection Gun. Smart and to the point! Kress USA Corporation.

Kruse, James A., et. al. Intraosseous Infusions: A flexible option for the adult or child with delayed, difficult, or impossible conventional vascular access. Critical Care Medicine 22: 728-729, 1994.

Precautions Necessary with Central Venous Catheters. FDA Drug Bulletin, Jul. 1989.

Valdes, Manuel M. Intraosseous Fluid Administration in Emergencies. Lancet, Jun. 11, 1977. pp. 1235-1236.

Iserson, Kenneth V. Intraosseous Infusions in Adults. Journal of Emergency Medicine 7: pp. 587-591, 1989.

Turkel, Henry. Emergency Infusion Through the Bone. Military Medicine. 149: pp. 349-350, Jun. 1984.

Glaeser, Peter W. Five Year Experience in Prehospital Intraosseous Infusions in Children and Adults. Annals of Emergency Medicine 22: pp. 1119-1124, Jul. 1993.

Selby, I. R. et. al., The intraosseous route for induction of anaesthesia. Anaesthesia 48: pp. 982-984, 1993.

Sawyer, Russel W. , et. al. The Current Status of Intraosseous Infusion . Journal of the American College of Surgeons.179: pp. 353-359, Sep. 1994.

Scott, Walter L. Complications Associated with Central Venous Catheters: A Survey. Chest 94: pp. 1221-1224, Dec. 1998.

* cited by examiner

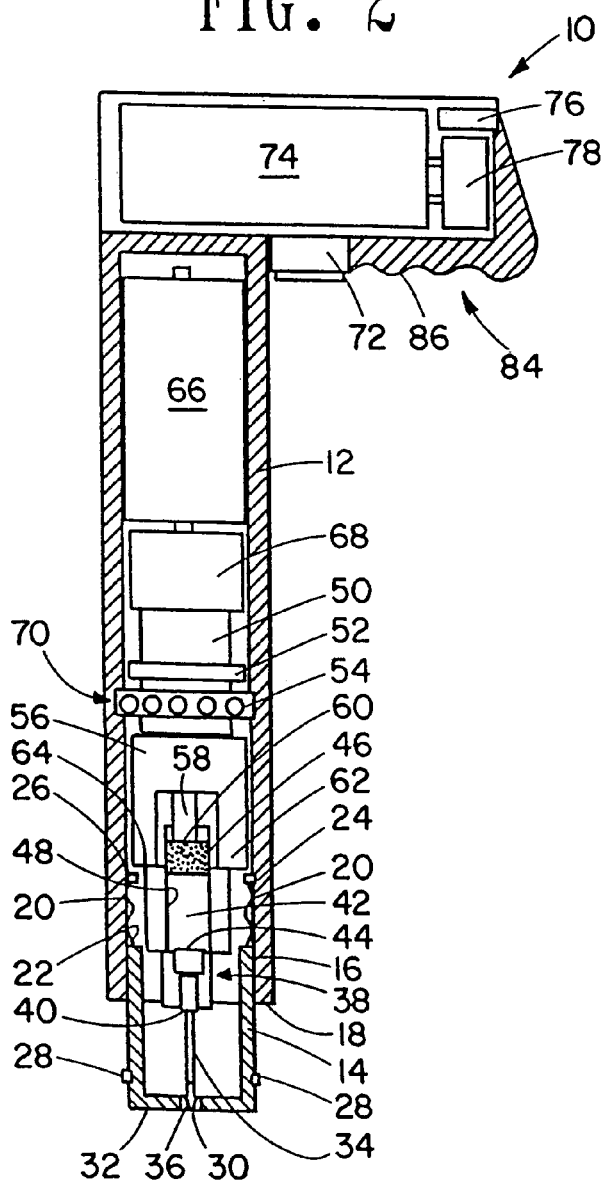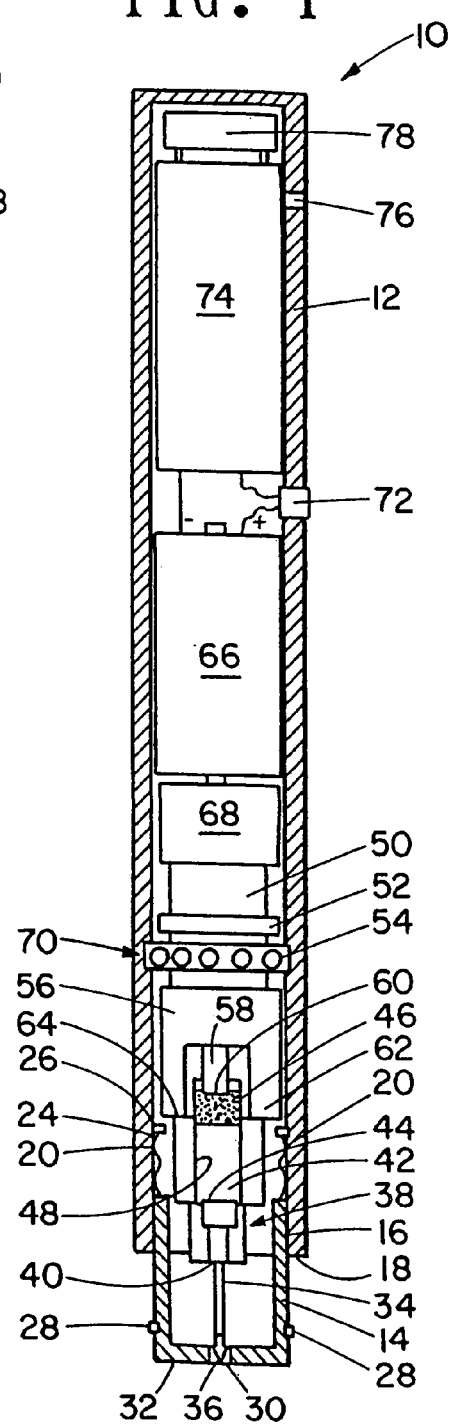

TISSUE PENETRATING DEVICE AND METHODS FOR USING SAME

This application is a continuation of U.S. patent application Ser. No. 09/757,122 filed Jan. 9, 2001, now U.S. Pat. No. 6,527,778, issued Mar. 4, 2003, which is a divisional of U.S. patent application Ser. No. 09/033,105 filed Mar. 2, 1998, now U.S. Pat. No. 6,183,442, issued Feb. 6, 2001.

BACKGROUND OF THE INVENTION

1. Field of the Invention

The present invention relates to a device for penetrating tissue and delivering bioactive agents thereto or extracting biological materials therefrom.

More particularly, the present invention relates to tissue penetration devices for delivering biologically active agents into tissue sites or extracting biological materials from the tissue sites where the device includes specially designed needles for penetrating a tissue site either rotationally or non-rotationally and specially designed delivery or extraction devices for controlled delivery of materials into tissue sites or extraction of materials from tissue sites.

2. Description of the Related Art

Accurate and effective tissue penetration and accurate and effective delivery of bioactive agents or extraction of biological fluids or material is regime of needle incorporating devices. Several patents have dealt with such needle incorporating devices including the following U.S. Pat. Nos. 1,523,068, 2,773,500, 2,773,501, 3,788,320, 3,811,442, 3,893,445, 4,666,438, 4,787,893, 4,969,870, 5,176,643, 5,271,744, and 5,312,364.

Although these patents generally relate to syringe and needle assemblies for the delivery of material into or extraction of material out of a tissue site, there is still a need in the art for new, efficient and controlled delivery and extraction devices incorporating new, efficient needles which reduce penetration time and improve penetration efficiency into sensitive tissue sites.

SUMMARY OF THE INVENTION

The present invention provides a device for delivering materials into or extracting materials from tissue sites. The device includes a fluid reservoir, a tissue penetrator or needle detachably engaging a first end of the reservoir and a plunger associated with the reservoir at its second end and designed to slidingly engage an interior surface of the reservoir. The device further includes at least one solenoid having a shaft detachably engaging a top of the plunger for moving the plunger within the reservoir, a power supply and associated circuitry for supply electrical power to the solenoid and at least one switch for controlling the solenoid. Preferably, the entire assembly is contained within a housing including a biased retractable tip protector (preferably, disposable) at its distal end having a penetrator. Additional solenoids can be used to control needle penetration speed and depth or to allow simultaneous or sequential infusion or removal of materials into or out of a tissue site.

The present invention provides a device for delivering materials into or extracting materials out of tissue sites. The device includes a reservoir/solenoid assembly as described above and additionally, a motor assembly for rotating the solenoid/reservoir assembly and at least one control switch with associated circuitry for activating the motor either in cooperation with the solenoid or independent from the switches and circuitry associated with the solenoid. Again, additional solenoids can be used to control needle penetration speed and depth by pushing against the motor assembly coordinated with needle rotation or to allow simultaneous or sequential infusion or removal of materials into or out of a tissue site.

The present invention also provides a tissue penetrator or needle including a hollow tubular member having a first end, a second end having a tissue penetrating tip associated therewith and at least one perforation therein located between a mid point of the hollow member and the tip end of the hollow member. The tissue penetrating tip includes two opposed cutting surfaces, each having a cutting edge, two opposed non-cutting surfaces and an opening associated with the tip at or near the apex. The hollow member can also include an enlarged region or seal for creating a seal between the penetrated tissue site and the penetrator.

This invention also provides a method for delivering material to a tissue site including positioning a tissue penetration device as described above in proximity to a tissue site to be penetrated, penetrating the tissue site with the penetrator, and activating the solenoid to deliver material into the tissue site from the reservoir of the penetration device or transfer material from the reservoir to the tissue site.

The present invention also provides a method for extracting material from a tissue site including positioning a tissue penetration device as described above in proximity to a tissue site to be penetrated, penetrating the tissue site with the penetrator, and activating the solenoid to extract material from the tissue site or transfer material from the tissue site to the reservoir.

This invention also provides a method for delivering material to a tissue site including positioning a tissue penetration device as described above in proximity to a tissue site to be penetrated, rotationally penetrating the tissue site with the penetrator, and activating the solenoid to transfer material from the reservoir to the tissue site.

The present invention also provides a method for extracting material from a tissue site including positioning a tissue penetration device as described above in proximity to a tissue site to be penetrated, rotationally penetrating the tissue site with the penetrator, and activating the solenoid to transfer material from the tissue site to the reservoir.

DESCRIPTION OF THE DRAWINGS

The invention can be better understood with reference to the following detailed description together with the appended illustrative drawings in which like elements are numbered the same:

FIG. 1 is a cross-sectional view of a first embodiment of the tissue penetration device of the present invention;

FIG. 2 is a cross-sectional view of a second embodiment of the tissue penetration device of the present invention;

DESCRIPTION OF THE PREFERRED EMBODIMENTS

Figure 3:
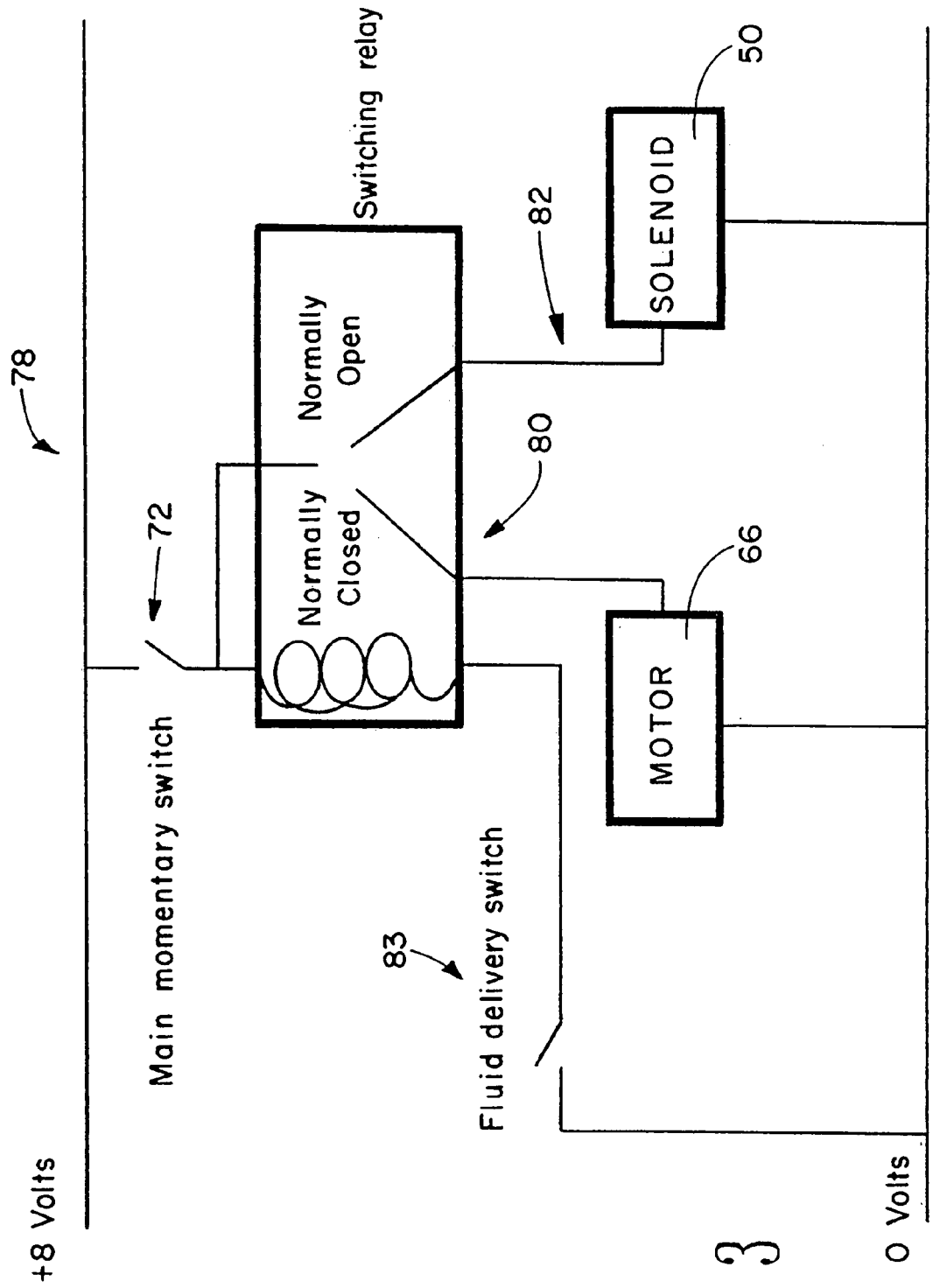
FIG. 3 is a schematic diagram of an embodiment of circuitry of the tissue penetration device of FIGS. 2 and 3.

The inventors have found that a device can be constructed for the efficient and controlled penetration of tissue sites and the subsequent controlled introduction of material into or extraction of material from a tissue site, i.e., transferring material into or out of a tissue site. Such a device, although having broad application in all tissue penetration applications, has special utility in hard tissue penetration applications such as bone, cartilage, tendon, ligaments or the like. The devices can be used on any animal, but is preferably designed for use with mammals and especially humans.

The device also allows for protection of health care providers from accidental needle pricks, while providing ease of operation and solenoid controlled introduction of materials into or extraction of materials from tissues sites. The device also incorporates a specially designed needle attached to a high speed motor for fast and easy penetration of hard tissues such as bone, cartilage, tendon, ligaments or the like The device can also be equipped with torque sensors associated with the motor so that the motor will automatically stop needle rotation when a given change in torque occurs such as when the needle transition from bone to soft tissue. The torque sensor and associated circuitry can also activate the solenoid either immediately after shutting off the motor or after a delay so that manual adjustments can be made prior to solenoid activation. Of course, motor power and solenoid power can be manually controlled either cooperatively or independently depending on the circuitry associated with the device or upon switch selections associated with the circuitry associated with the device.

The present invention discloses a new device and methodology for use in accurate tissue penetration and delivery of materials (bioactive material such as medications, fillers, tags or tracking agents, implants, or the like) into a tissue site or extraction of materials (bodily fluids, biopsies, tissues samples, bone marrow or the like) from a tissue site.

For example in marrow aspiration, the device would be placed on (in contact with) the bone cortex and the tissue penetrator member or needle, which resides at the device's distal end, would be rotated by the motor until it penetrates the cortical bone to a pre-determined depth. The penetration depth can either be adjusted by an adjustable depth stop or by having the motor sensor automatically shut the motor off when a turning torque for the needle indicates full penetration of the bone cortex (sudden drop in turning torque). At that instance, the solenoid (or similar electrically activated retraction device) in a "pull" configuration is either manually or automatically activated or powered up and bone marrow is aspirated into the needle's hollow shaft through orifices or perforations in the shaft and/or through an opening in the needle tip. The material travels through the needle and is accumulated in the device's storage reservoir.

In this example, the penetrator rotates without linear translation or extension with penetration pressure being supplied by the user. Once appropriate penetration (and thus tip positioning) is achieved, power to the motor is manually or automatically discontinued and power to the solenoid is initiated either manually or automatically. The solenoid then retracts and aspirates (removes) material from the tissue site or pushes out and delivers materials to the tissue site. The device can be easily fabricated at a low cost.

Applications

The devices of the present invention can be used for a number of medical applications, including, without limitation, the following:

1. Intra-joint Fluid Aspiration:

The penetrator or needle of the device is driven into a tissue site without rotation by a solenoid in a push condition (sometime referred to as a "push" solenoid). Once the needle tip is at the desired location, a second solenoid in a pull condition (sometimes referred to as a "pull" solenoid) is used to aspirate or remove material such as fluid from the tissue site. In this embodiment, the device does not need to have a motor. This embodiment and use of the device allows for extraction of synovial fluids, e.g., to quantify the presence of metallo-proteases or other markers of osteoarthritis, of blood or fluids to alleviate joint pressure, blood to perform culture studies or the like.

2. Intra-joint Delivery Device:

Similarly, a "push" solenoid lets the needle penetrate the joint in a linear fashion. Once the desired penetration is accomplished, a mechanical stop acts as an electrical switch for a second "push" solenoid, which applies positive pressure on the plunger of the syringe (reservoir) until all of its contents (such as bioactive agents) are released (delivered) into the joint. In this embodiment, the device also does not need to have a motor. This embodiment and use of the device allows for delivery of anti-inflammatory drugs and/or painkillers (e.g., lidocaine) or of articular cartilage surface coating fluids (e.g., hyaluronic acid, anti-arthritic agents) or the like.

3. Intraosseous Delivery of Drugs or Bioactive Agents:

An example is the delivery of drugs, pharmaceuticals, growth factors, etc. inside the marrow cavity of a bone. For example, if a drug needs to be delivered in the marrow cavity of the antero-medial diaphyseal portion of the tibia, or in a tibial metaphysical portion, the device is positioned perpendicularly on the skin over the region of the bone to be penetrated. As the user applies some pressure on the device, the penetrator (preferably a needle of the paddle-tipped hollow needle design described herein) protrudes from the housing through the septum associated with the tip protector, cuts through the skin and rests on the periosteum. The user switches the motor on and the needle penetrates through the cortex, until a mechanical stop is reached (say after a 15 mm penetration). The mechanical stop then acts as an electrical sensor and/or switch, which selectively turns the motor off and powers up or activates the solenoid. The solenoid then pushes out and applies a compressive force on the plunger of the syringe. The drug is pushed out through the orifices placed on the lateral aspects of the needle and/or through the opening in the center of the needle tip. Of course, the motor activation can be controlled by sensors associated with the device. One sensor could determine when bone contact has occurred (pressure sensor), while other sensors could determine when a change in torque has occurred which would indicate a transition from a bone type medium to a soft tissue medium or a less bone-like medium depending on the nature of the torque sensors.

The devices of the present invention do not depend on developing large momentum or subsequent impact to achieve penetration as do many prior art devices. The devices of the present invention penetrate by developing large strains locally in bone close to the interface with the cutting edges of the penetrator. As a result, this method completely eliminates the possibility of fracturing bone as may be the case in momentum or impact tissue penetration devices. The devices of the present invention also allows for proper controlled delivery of materials into a tissue site reducing if not eliminating delivery until a desired penetration is achieved.

Fluid delivery, moreover, does not depend on inertial forces developed due to impact. Because it is difficult to control the inertial force in the syringe fluid in momentum-based delivery systems, it is difficult to consistently deliver the same amount of fluid every time to a given tissue site. In the devices of the present invention, fluid delivery is much more controlled making uniform and consistent administration of materials to a tissue site routine. This uniformity and consistency is accomplished through the use of solenoid (or a similar) delivery systems, which delivers or extracts the same amount of material every time because the solenoid uses the same amount of electrical energy and force profile during administration as opposed to user administration.

4. Intracranial Pressure Release:

In traumatic head injuries, swelling due to fluid adjacent to the brain may develop which can lead to death or brain damage. Such fluid build up can be relieved using the devices of the present invention by penetrating the cranium in the vicinity of the site of injury. Once penetration of the cranium is achieved by drilling through the cranium with the penetrator or needle, the motor automatically stops (this is accomplished by shutting down the power to the motor when a reduction of motor-torque is detected either manually or automatically). After drilling, the needle can be further inserted into the soft tissue inside the cranium using user-applied force until a desired penetration depth is achieved. A "pull" solenoid can then pull the plunger of the syringe thus creating negative pressure that will aspirate the excess fluid into the reservoir.

5. Intracranial Delivery of Bioactive Agents:

The devices of this invention can also be used to deliver medication such as cancer drugs to brain tumors. As in application 4, the device penetrates the cranium and stops immediately when the needle contacts intracranial soft tissue (torque change on the needle). The user continues to apply a small compressive force and thus the needle travels into the soft tissue. When a desired penetration is achieved, a mechanical stop brings the needle to a stop and also closes the solenoid circuit. A "push" solenoid pushes the plunger of the syringe until all fluid contents of the syringe are delivered inside the tumor. This process can be adjusted to proceed at any given rate from very fast delivery to very slow delivery. Although the delivery of anti-cancer agents may require fast delivery, the administration of medications to ameliorate the adverse effects of brain injuries such as calpain inhibitors or growth promoters may require slow continuous administration.

6. Marrow Extraction:

The devices of the present invention can also be used to access the marrow cavity of a given bone. Using a "pull" solenoid, we can create a vacuum in the syringe which will aspirate a desired amount of marrow fluid. Examples of extraction are: bone marrow is aspirated for transplantation for cancer patients or marrow is aspirated to obtain mesenchymal stem cells or other cells to be used in cell-based transplantation therapies.

7. Spinal Fluid Extraction:

A similar technique as described in 6 above can be used to aspirate spinal fluid. A double solenoid can be used, where one pushes the syringe into a proper position and another solenoid pulls and thus aspirates the fluid out.

8. Compartment Syndrome:

Similarly, this system can be used to relieve pressure developed in a compartment syndrome.

The devices of the present invention should preferably have a disposable distal end because the distal surface comes in contact with skin and may become contaminated with bodily fluids (e.g., blood) that may potentially exude through the penetration orifice and carry viral or bacterial infections. The device also is equipped with a septum protected needle to aid in preventing needle pricks because the needle before and after use is protected within the retractable and preferably disposable tip protector. The device can include custom made battery packs and chargers preferably waterproof, made of medical grade materials, and preferably include sensor that will monitor and indicate battery charge. The devices can have different heads (distal ends) which allow or permit different needle penetration depth and/or have sensors to measure needle to tissue pressure. Penetration depth control can be achieved by having mechanical stops on the retractable tip. Needles of various size and gages can be used as well. The device, moreover, can be used to implant small microdevices into tissue sites and even for screwing threaded bone pins into bone site to repair fractures.

Paddle-Tipped Hollow Needle

The inventors have also found that a new needle tip design can greatly facilitate penetration of hard tissue such as bone with reduced ancillary bond injury or fracturing. The needle is of a paddle-tipped hollow design. The needle includes two opposing cutting surfaces with cutting edges off the perpendicular and two opposed non-cutting surfaces. The needle tip is generally in the form of a quadrilateral (rectangular or parallelogram) with cutting surfaces associated with its short sides and non-cutting surfaces associated its long sides. The tip has a first interior angle that is generally less than 90° (rectangular) and greater than about 0° (linear) and a second interior angle which is 180° minus the first angle. Preferably, the first angle is between about 80° and about 10°, more particularly the first angle (which is an acute angle) is between about 80° and about 50°, and especially the first angle is between about 80° and about 60°, with 70° being particularly preferred. As shown in the diagrams (FIGS. 9 and 14), this needle has a shape that allows it to act as a drill bit and thus penetrate bone with ease, when rotating clockwise. Of course, a mirror image construction would allow the needle to cut in a counterclockwise direction.

Figures 12, 13, 14, 15, 16:
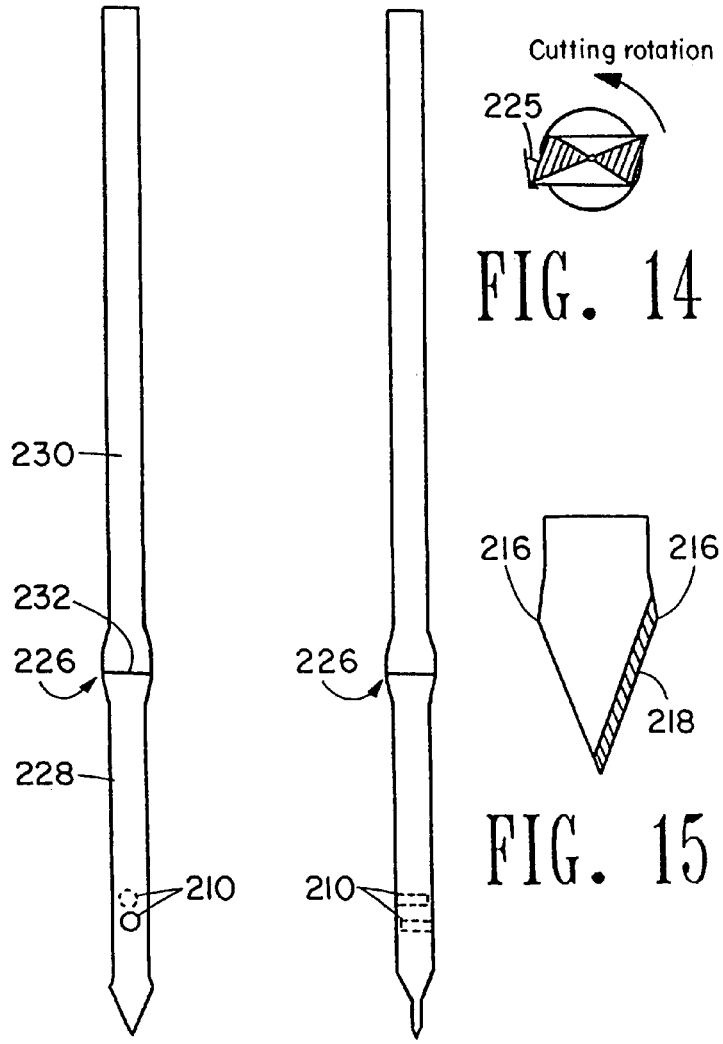
FIG. 12 is a front plan view of a second embodiment of a tissue penetration member of the present invention.
FIG. 13 is a side plan view of the member of FIG. 12.
FIG. 14 is a top plan view of a tip of the member of FIG. 12.
FIG. 15 is a front plan view of the tip of FIG. 14.
FIG. 16 is a side plan view of the tip of FIG. 14.

The needle design has the following features: (1) the needle design eliminates friction between needle surface and bone, thus, it decreases time of penetration and thermal damage to the bone; (2) the needle has two cutting edges on the two thin sides of flat triangular profiled surfaces; (3) on the proximal end there is a taper to enlarge the diameter of the needle shaft to match the hole size created by the paddled bit in order to seal the fluid and prevent leaking on injection (FIG. 12); (4) the needle production will require only a minor change in the fabrication scheme that is already followed for existing needles. The taper can be an optional, separate piece that can be pressed onto the shaft of the needle at any position along the length of the shaft; (5) in the intracranial applications, where bone abuts against soft tissue, it may be desirable not to use a rotating needle to avoid excessive soft tissue damage. This can be accomplished by the following scheme: The needle is powered by the motor which rotates and thus the needle penetrates the bone. The motor torque (i.e., the resistance offered by the bone) is monitored until a sufficiently large drop is observed. At that point, the distal end of the needle has drilled through the bone such as the cranium and about to enter soft tissue. At that point, the motor is automatically turned off and through a simple push by the user the needle can now continue its penetration in a linear manner (i.e., without rotation). This linear translation continues until the mechanical stop is reached at which point the "pull" or "push" solenoid pushes or pulls the syringe plunger and thus delivers or aspirates fluids.

Referring now to FIG. 1, a first embodiment of a tissue penetration device of the present invention, generally 10, is shown. The device includes a housing 12 which can be made of any medical approved material, but is generally made of a medically approved plastic. The housing 12 can be of a generally cylindrical shape or can be shaped to conform to a users hand. Of course, any shape is acceptable, provided that the shape does not significantly adversely affect the function of the device. It should be recognized, moreover, that the housing can be constructed out of a single material or a mixture of materials, can be an integral structure or can be constructed of detachable elements as well be described more fully herein.

The device 10 further includes a retractable cap 14 which slidingly engages an interior surface 16 of housing 12 at its distal end 18. The cap 14 is biased by a bias member 20 which has a first end 22 associated with the cap 14 and a second end 24 associated with a contact switch 26 for initiating fluid ejection. The cap 14 also includes a user adjustable depth stop 28 and a needle penetrable membrane 30 associated with its bottom surface 32 which is placed in contact with a patient during use.

The device 10 further includes a needle 34 positioned with in the device 10 so that its tip 36 is poised to penetrate the membrane 30. The needle 34 is detachably or fixedly attached to a needle holder 38 at its opposite end 40. The holder 38 is associated with a fluid reservoir 42 and forms the reservoir's needle end 44. The reservoir 42 has a plunger 46 which slidingly engages an interior surface 48 of the reservoir 42. The plunger 46 acts to either force fluid out of the reservoir or suck fluid into the reservoir depending on whether the device is being used to delivery material to a tissue site or withdraw material from a tissue site.

The device 10 further includes a solenoid 50, an electrical contact bushing 52, a bearing 54, a solenoid/needle coupler 56 and a solenoid shaft 58. The shaft 58 has a distal end 60 is either fixedly or detactably attached to or associated with a top of the plunger 46 so that the plunger 46 can be moved vertically within the reservoir 42. If the shaft 58 is fully extended prior to use, then the solenoid 50 will retract the shaft 58 and the device 10 will act to remove material from the tissue site. If the shaft 58 is fully retracted, then the solenoid 50 will extend the shaft 58 and the device 10 will act to inject material into the tissue site. The coupler 56 has a lip 62 that contacts a top edge 64 of the reservoir 42. The lip 62 allows the reservoir 42 and associated needle assembly to be pushed downward so that needle penetration can be controlled by the solenoid 50 instead of being controlled manually. Of course, the depth and rate of penetration as well as the rate to removal can be manually controlled or controlled by a second solenoid (not shown).

The device 10 further includes a high speed DC motor 66 and a motor/solenoid coupler 68. The motor allows the entire solenoid/reservoir/needle assembly to be rotated so that the needle can drill into hard tissues such as bone. The bearing 54 is positioned within a groove 70 in the housing 12 so that the solenoid/reservoir/needle assembly can be rotated relative to the housing 12.

The device 10 further includes an on/off switch 72, a battery 74, battery charging ports 76 and a relay circuit 78. A preferred electrical communication schematic for the operation of the device 10 using the switch 72, battery 74 and relay circuit 78 is shown in FIG. 3. The device 10 operates on an 8 V system, although any other voltage can be used as well provided that the voltage and current meet design and safety criteria of the device. The circuit 78 is designed so that a motor circuit 80 is normally in a closed condition, while a solenoid circuit 82 is normally in a open condition. If the device 10 is set up to operate so that fluid ingress or egress occurs automatically after rotatory penetration into a tissue site, then the circuit 78 will automatically open the motor circuit 80 after penetration and close the solenoid circuit 82. The plunger 46 is either retracted or extended depending on the initial state of the shaft of the solenoid via a fluid switch 83.

Referring to FIG. 2, a second configuration of the device 10 of FIG. 1 is shown. The main structural difference between the device of FIG. 1 and the device of FIG. 2 is the arrangement of the switch 72, the battery 74, the battery charger ports and the circuit 78 which are contained within a pistol grip 84 which extends out substantially horizontally from the housing 12. The grip 84 can be integral with the housing 12 or can attachably or detachably engage the housing 12. The switch 72 is position in a lower surface 86 of the grip 84 so that a user can easily switch the device on and off through finger pressure.

Figure 4:
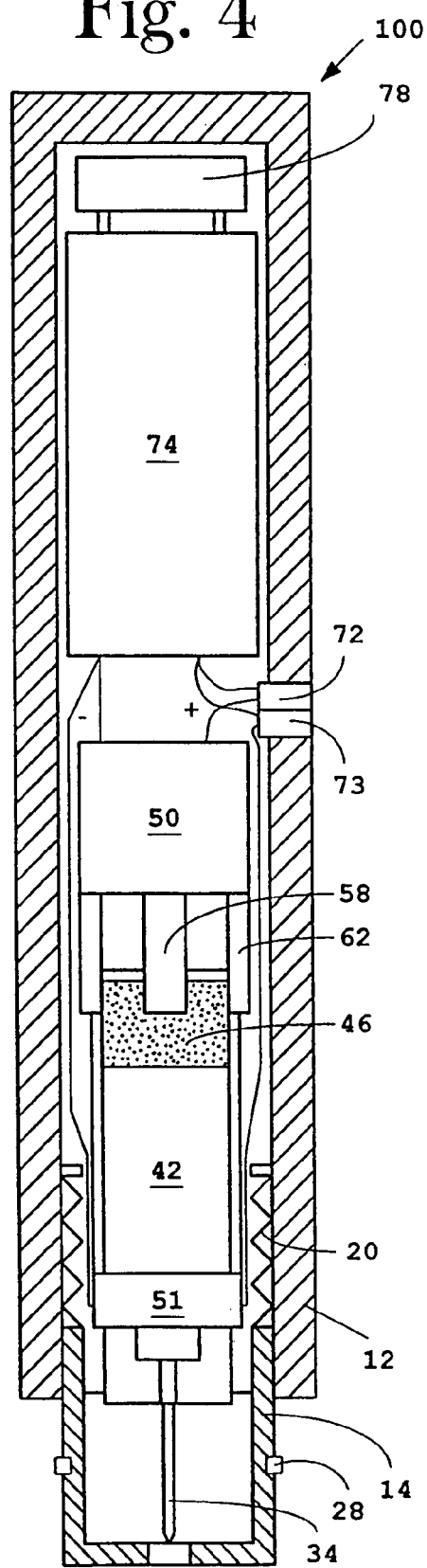
FIG. 4 is a cross-sectional view of a third embodiment of the tissue penetration device of the present invention.
Figure 5:
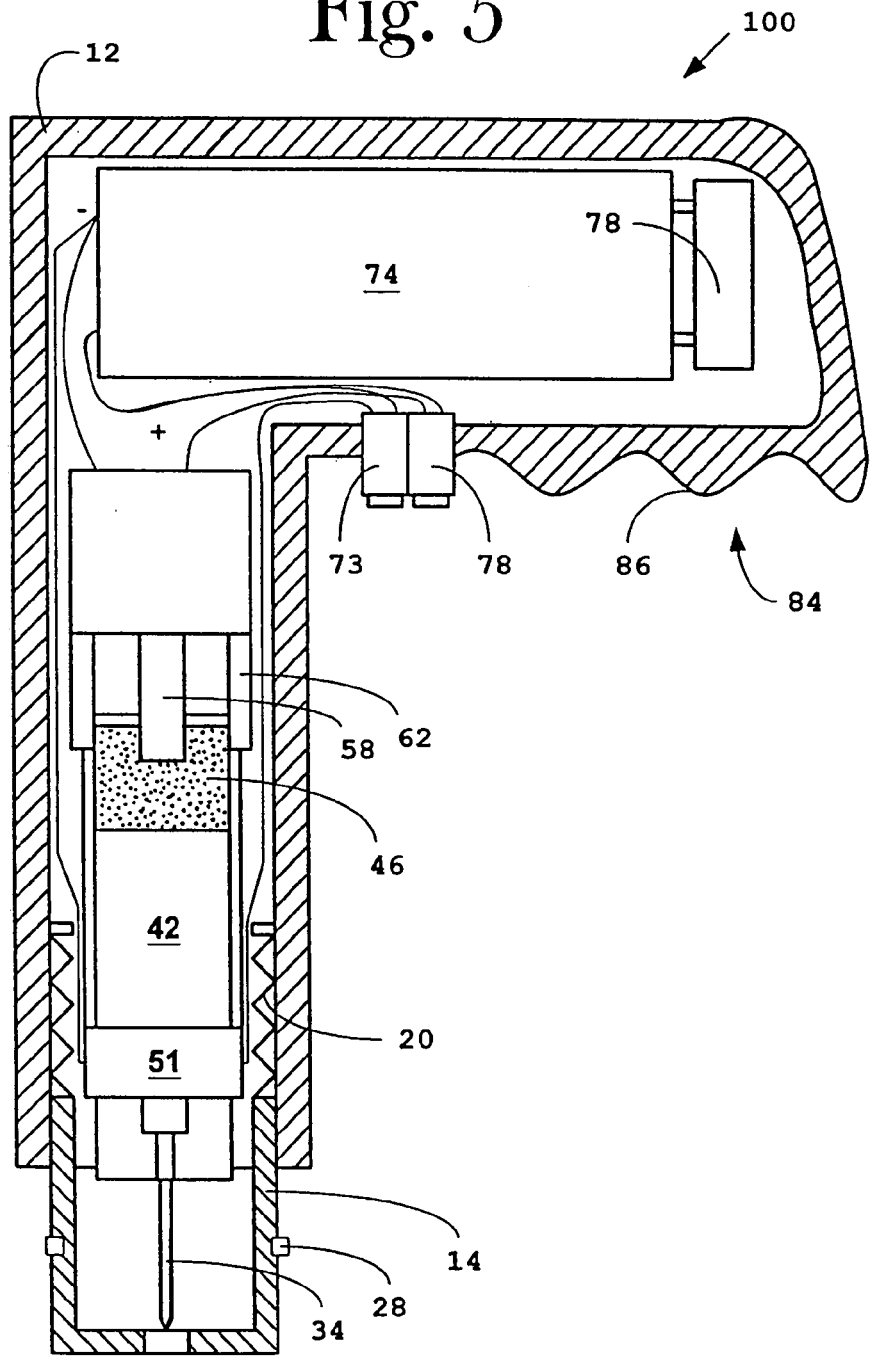
FIG. 5 is a cross-sectional view of a fourth embodiment of the tissue penetration device of the present invention.

Referring to FIGS. 4 and 5, a third and fourth embodiment of the device, generally 100, of the present invention which are similar to the device 10 of FIGS. 1 and 2, respectively, without the inclusion of the motor and bushing/bearing assembly of the device 10. These latter embodiments are used primarily in procedures where on vertical force is necessary for tissue penetration and no rotatory drilling is required. The circuitry associated with these latter embodiments is simplified by the absence of the motor and, thus, the switch 72 can be used to directly turn on and off the solenoid 50. The device 10 further includes a second solenoid 51 to control the rate the depth of penetration of the needle 34. The second solenoid 51 is controlled by a on/off second switch 73.

Figure 6:
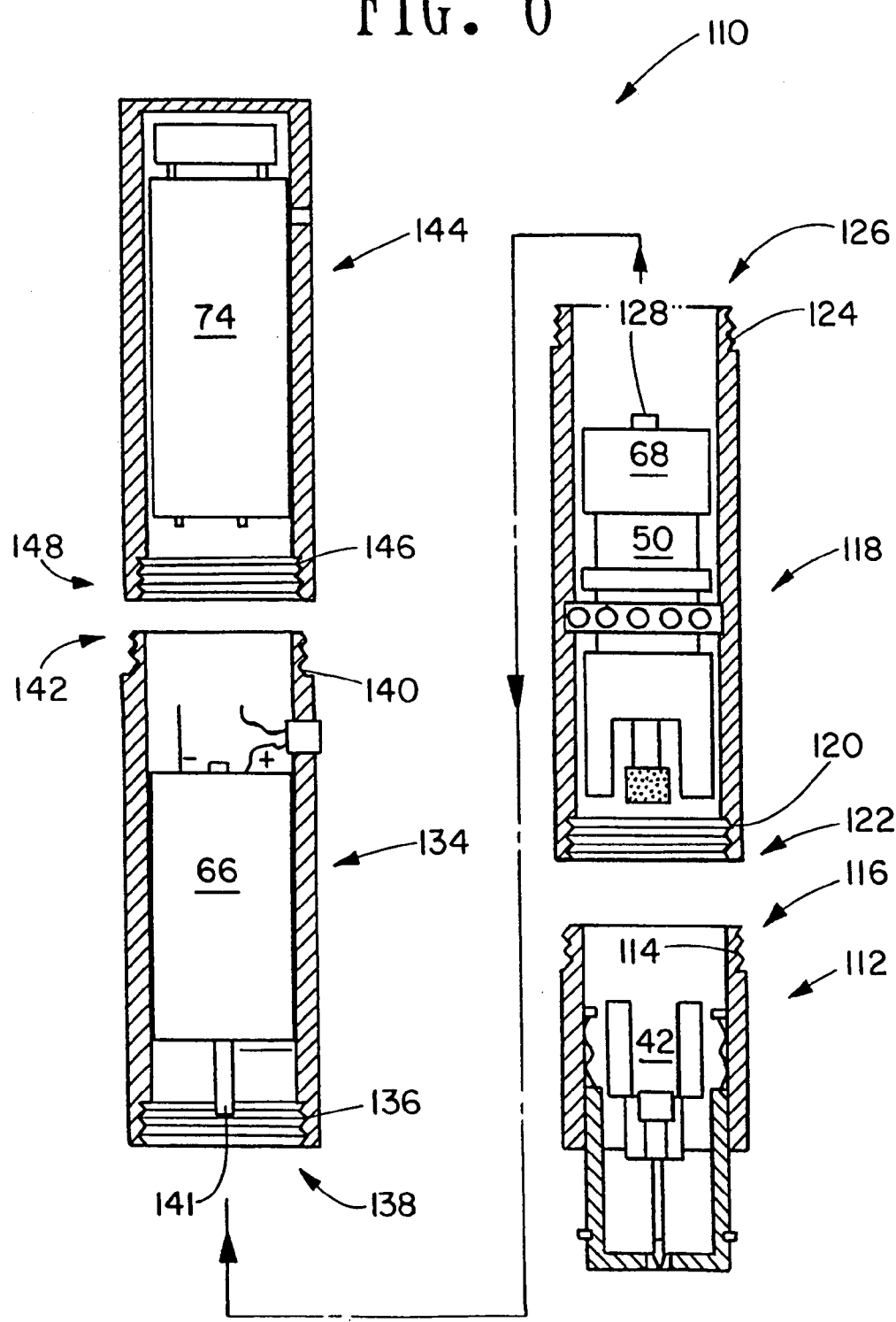
FIG. 6 is a cross-sectional view of a fifth embodiment of the tissue penetration device of the present invention.

Referring now to FIG. 6, yet another embodiment of tissue penetration device of the present invention, generally 110, includes a three or four part detachable construction of the device of FIGS. 1 and 2. The device 110 includes a reservoir/needle assembly 112 shown with a male threaded connection 114 at its proximal end 116. The device 110 also includes a solenoid assembly 118 having a female threaded connection 120 associated with its distal end 122 and designed to threadingly engage the male connector 114. The solenoid assembly 118 also has a male threaded connection 124 associated with its proximal end 126 and a rotatory shaft receiver 128. Of course, the solenoid assembly can be subdivided into a solenoid/needle coupler subassembly which includes the plunger 46, a bushing/bearing subassembly and a solenoid subassembly. These subassemblies can be attached by threaded connection, snap connections or any other attachment mechanism. Additionally, the devices of the present invention can include one or more solenoid where the other solenoid can be associated with the needle for controlled tissue penetration.

The device 110 also includes a motor assembly 134 which includes the motor and a female threaded connection 136 associated with its distal end 138 and designed to threadingly engage the male connector 124 and a male threaded connection 140 associated with its proximal end 142 and a rotatory shaft 141. The device finally includes a battery assembly 144 having a female threaded connection 146 associated with its distal end 148 and designed to threadingly engage the male connector 140. Of course, the battery assembly 144 includes the battery, the switch and the relay circuit and can be vertically disposed or positioned or horizontally disposed or positioned relative to the other assemblies to produce the assembled devices depicted in FIGS. 1–2 or 4–5 depending on the desired subassemblies to be associated with the final device.

Although the assemblies shown in FIG. 6 are connected by threaded connections and modularized in the manner shown, the device of the present invention can be modularized in any other procedure and the modular components can be connected by any other connection means known in the art such as quick connects, threaded locking connections, snap-on connections, permanent or removable adhesive bonding, or any other method of connecting modular sections together.

Figure 7:
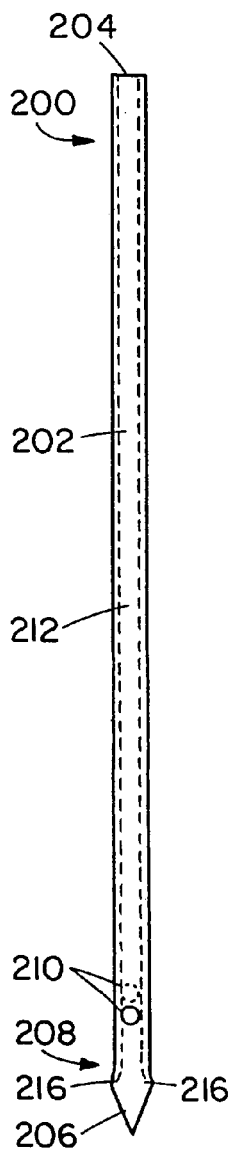
FIG. 7 is a front plan view of a first embodiment of a tissue penetration member of the present invention.
Figure 8:
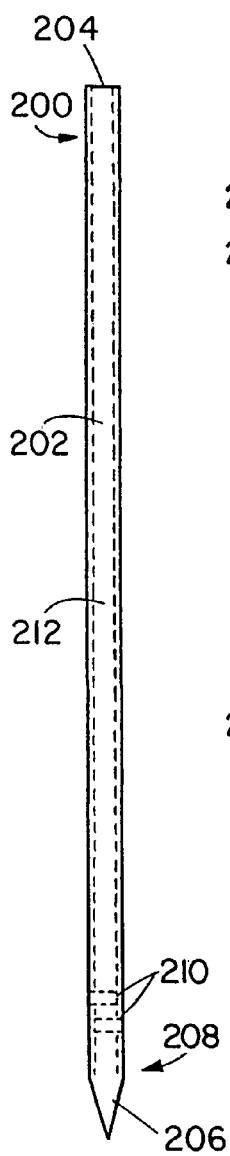
FIG. 8 is a side plan view of the member of FIG. 7.

Referring now to FIGS. 7–11, a first embodiment of a new tissue penetrator or needle, generally 200, is shown. The penetrator 200 includes a substantially cylindrical hollow tube 202 having a proximal end 204 and a tip 206 associated with its distal end 208. The needle 200 also includes two apertures or perforations 210 so that an interior 212 of the tube 202 can be brought into fluid communication with a tissue site through the apertures 210. The tip 206 is paddle shaped having a V-shaped profile as viewed from the front (FIG. 7) and a tapered V-shape when view from the side (FIG. 8). The tip 206 has two cutting edges 214 and preferably has two raised portions 216 where the tip 206 and the tube 202 transition one into the other and an aperture 215 located at or near its apex.

Figure 9:
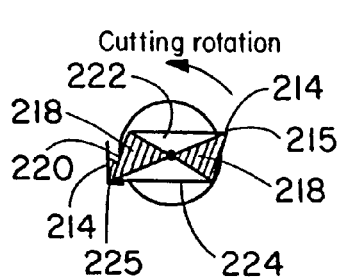
FIG. 9 is a top plan view of a tip of the member of FIG. 7.
Figure 10:
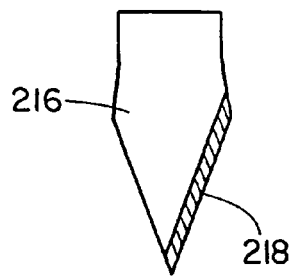
FIG. 10 is a front plan view of the tip of FIG. 9.
Figure 11:
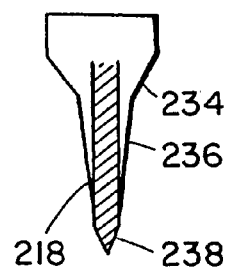
FIG. 11 is a side plan view of the tip of FIG. 9.

As shown FIG. 9, the tip 206 is in the shade of a parallelogram with cutting surfaces 218 associated with a smaller pair of sides 220 and non-cutting surfaces 222 associated with a larger pair of sides 224. The tapered V-shaped configuration of the tip 206 is generally achieved by pressing the tip 206 and then grinding the cutting surfaces 218 so that the cutting edges 214 will have a cutting angle 225 which has an especially preferred value of 70°. The raised portions 216 are designed to ensure that the hole drilled into the bone is of a diameter slightly greater than the diameter of the outside diameter of the tube 202. For example, if the tube 202 has an outside diameter of about 1.27 mm, then the diameter of the tip 206 at the raised portions 216 would be about 1.50 mm. Of course, all that is really required is that the diameter at the raised portion 216 be slightly greater than the diameter of the tube 202 so that no resistance will accompany further insertion of the needle 200 after bone penetration.

Referring now to FIGS. 12–16, a second embodiment of a new needle 200 of the present invention can be seen to include the same elements as above, with the addition of a bone seal 226. The bone seal 226 is a flanged out portion of the tube 202 and it located a given distance from the perforations 210. If the entire needle is about 38 mm in height and has an o.d. of about 1.27 mm and the perforations 210 are relatively close to the raised portions 216 of the tip 206, then the bone seal 226 is preferably located about 7 mm above the apertures 210. Of course, the each location of the seal 226 will depend on the use to which the needle will be put and the depth of penetration desired. As is shown in FIGS. 12 and 13, the tube 202 is shown as two distinct pieces 228 and 230 each having a mating flange 232. The two pieces 228 and 230 can be integrally formed out of a single piece of material or can be made of out separate pieces of material than have been fixedly attached either by bonding, welding, fusing, fitted or by any other technique known in the art whereby two pieces can be joined together to form a single piece structure capable of operating as a single unit.

The tapered V-shaped side view of the tips 206 of the needles of FIGS. 7 and 12 can be seen to include at least three different tapering regions 234, 236 and 238. The first region 234 is associated with the pressing process that formed in the tip into a generally rectangular shape from the cylindrical shape of the tube. The second and third regions 236 and 238 are associated with the tip forming process and cutting edge forming process so that a parallelogram configuration is achieved. Thus, the cutting surfaces of the needle have a tapered V-shape as well.

Although the tip is shown as a parallelogram shape having two opposed cutting surfaces and edges, the present invention also contemplates other polygonally shaped tips including rectangular with two cutting surfaces, pentagons with two or three cutting surfaces, hexagons with three cutting surfaces, etc. where the sides of the polygons are not equal so that the cutting edges are associated with smaller sides of the polygonal shape and can have sharp well defined cutting edges.

EXAMPLES

The following examples are included for the sake of completeness of disclosure and to illustrate the methods of making the compositions and composites of the present invention as well as to present certain characteristics of the compositions, but in no way are these examples included for the sake of limiting the scope or teaching of this disclosure.

Figure 17:
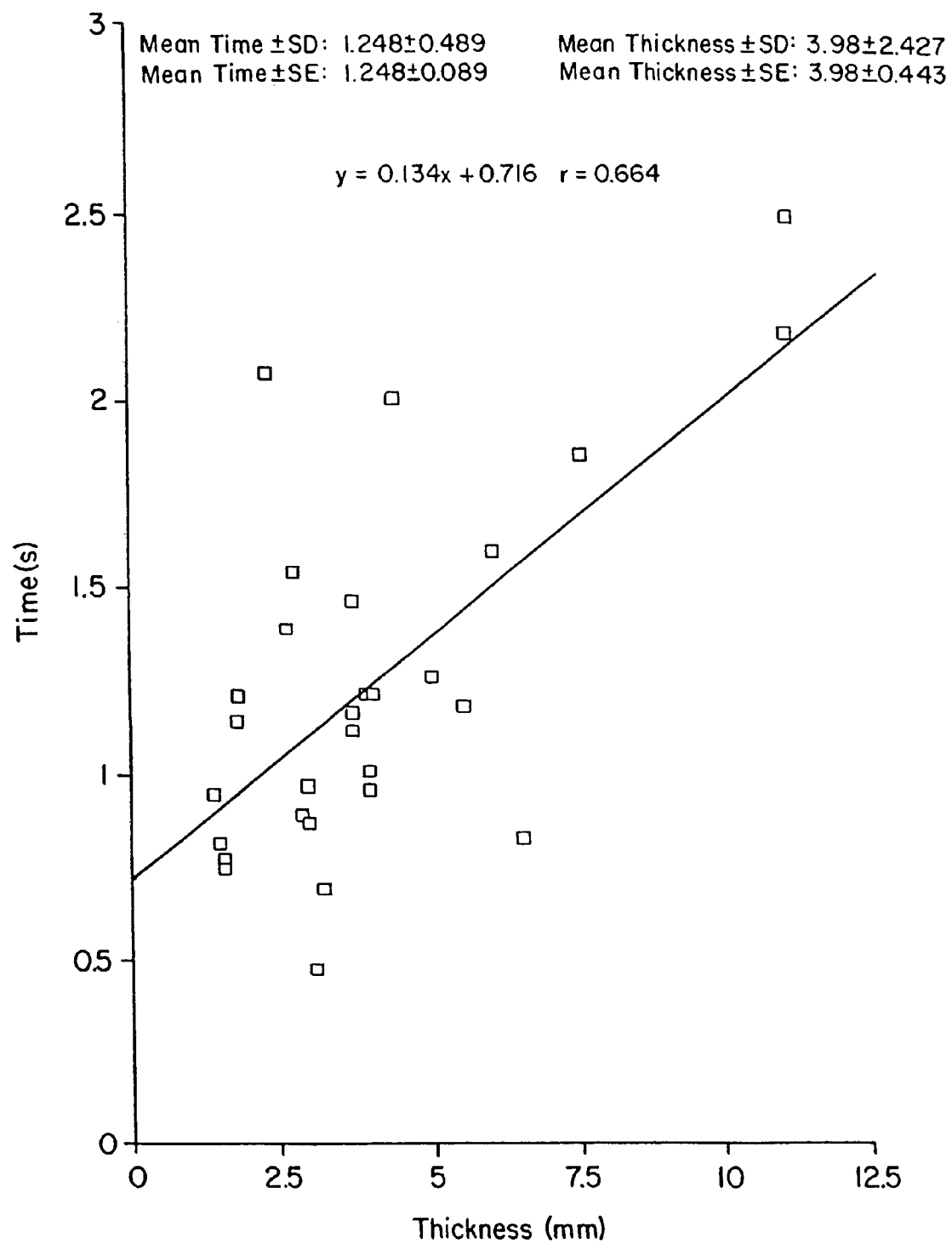
FIG. 17 is a graph depicting penetration time versus bone thickness data for the tissue penetration device of this invention.

In preliminary experiments using a prototype device of the present invention using the new needle configuration, the inventors were able to achieve complete penetration of cortical bone in 100% of the cases in 1.3 seconds while the whole process currently takes approximately 2 to about 2.5 seconds (injection or removal of material). The inventors also analyzed time of full penetration plotted against cortical thickness as shown in FIG. 17. The data shown in FIG. 17 demonstrates the penetration of bone up to 12.5 mm in thickness can be accomplished in under 2.5. The data was shown to have a correlation of y=0.134x+0.716 with a r value of 0.664. The mean time was 1.248 for a mean thickness of 3.98. The existing prototype demonstrates that the devices of this invention allow for fast bone penetration and delivery or extraction using a solenoid to affect delivery into or extraction from a tissue site.

All United States patents, all foreign patents and all articles cited therein are incorporated herein by reference as if each was incorporated by reference at the time of introduction. Although the invention has been disclosed with reference to its preferred embodiments, from reading this description those of skill in the art may appreciate changes and modification that may be made which do not depart from the scope and spirit of the invention as described above and claimed hereafter.

We claim:
1. An apparatus comprising:
   a. a tissue penetrator disposed in a distal portion of the apparatus;
   b. a solenoid for controlling penetrator penetration speed and depth;
   c. a motor adapted to rotate the solenoid and the penetrator,
   d. a power supply and associated circuitry for supplying electrical power to the solenoid;
   e. a switch for starting and stopping the solenoid;
   f. a housing surrounding the penetrator, the solenoid and the power supply; and
   g. a disposable, biased retractable protector having a septum at its distal end and a bias member,
   where the protector is detachably connected to a distal end of the apparatus and protects a tip of the penetrator and where electric power supplied to the solenoid allows the penetrator to penetrate a tissue site at a controlled rate and to a controlled depth.

2. The apparatus of claims 1, wherein the penetrator comprises a hollow shaft, an aperture and a tip having a quadrilateral cross-section, where the quadrilateral includes two opposed short sides and two opposed long sides and where the short sides comprise cutting surfaces and long sides comprise non-cutting surfaces.

3. The apparatus of claims 2, wherein the quadrilateral is a parallelogram.

4. The apparatus of claim 1, wherein the bias member allows the protector to move relative to the penetrator so that the penetrator penetrates the septum and extends into the tissue site to the controlled depth when the apparatus is in use and to move back after use.

5. The apparatus of claim 1, further comprising:
   a torque sensor adapted to sensor changes in a motor torque, where the power supply supplies power to the sensor and the circuitry turns the motor off when a change in torque evidences a transition from hard tissue to soft tissue.

6. An apparatus comprising:
   a. a housing;
   b. a solenoid mounted in a middle portion of an interior of the housing;
   c. a power supply and associated circuitry mounted in an upper portion of the interior of the housing and connected to the solenoid for supplying electrical power to the solenoid;
   d. a motor mounted in the interior of the housing and connected to the power supply;
   e. a torque sensor adapted to sensor changes in a motor torque,
   f. a tissue penetrator disposed in a distal portion of the interior of the housing and connected to the solenoid;
   g. a switch for starting and stopping the solenoid; and
   h. a disposable, biased retractable protector having a septum at its distal end for protecting a tip of the penetrator,
   where electric power supplied by the power supply to the solenoid in a push mode pushes the penetrator into a tissue site including bone at a controlled rate and to a controlled depth and where electric power supplied by the power supply to the solenoid in a pull mode pulls the penetrator from the tissue site at a controlled rate, and where electric power supplied by the power supply to the motor and the circuitry controls a motor speed and a motor direction, and where electrical power supplied to the torque sensor and the circuitry turns the motor off when a change in torque evidences a transition from bone to soft tissue.

7. The apparatus of claim 6, wherein the bias member allows the protector to move relative to the penetrator so that the penetrator penetrates the septum and extends into the tissue site to the controlled depth when the apparatus is in use and to move back after use.

8. The apparatus of claim 6, wherein the tissue site comprises a cranium.

9. The apparatus of claims 6, wherein the penetrator comprises a hollow shaft, an aperture and a tip having a quadrilateral cross-section, where the quadrilateral includes two short sides and two long sides disposed in an alternating configuration so that the short sides and longs sides are opposed and where the short sides include cutting surfaces and long sides are non-cutting surfaces.

10. The apparatus of claims 9, wherein the quadrilateral is a parallelogram.

11. An apparatus comprising:
    a. a housing;
    b. a power supply and associated circuitry mounted in an upper portion of the interior of the housing;
    c. a motor mounted in the interior of the housing and connected to the power supply;
    d. a torque sensor adapted to sensor chances in a motor torque,
    e. a solenoid mounted in the interior of the housing and connected to the power supply;
    f. a tissue penetrator disposed in a bottom portion of the interior of the housing;
    g. a switch for starting and stopping the motor and the solenoid; and
    h. a disposable, biased retractable protector having a septum at its distal end for protecting a tip of the penetrator,
    where electric power supplied by the power supply to the motor rotates the penetrator at a controlled rate either in a cutting direction or a retracting direction and where electric power suppled by the power supply to the solenoid in a push mode pushes the penetrator into a tissue site including bone at a controlled rate and to a controlled depth while the motor rotates the penetrator in the cutting direction and where electric power supplied by the power supply to the solenoid in a pull mode pulls the penetrator from the tissue site at a controlled rate while the motor rotates the penetrator in the retracting direction, and where the electrical power supplied to the torque sensor and the circuitry turns the motor off when a change in torque evidences a transition from bone to soft tissue.

12. The apparatus of claim 11, wherein the bias member allows the protector to move relative to the penetrator so that the penetrator penetrates the septum and extends into the tissue site to the controlled depth when the apparatus is in use and to move back after use.

13. The apparatus of claim 11, wherein the tissue site comprises a cranium.

14. The apparatus of claims 11, wherein the penetrator comprises a hollow shaft, an aperture and a tip having a quadrilateral cross-section, where the quadrilateral includes two short sides and two long sides disposed in an alternating configuration so that the short sides and longs sides are opposed and where the short sides include cutting surfaces and long sides are non-cutting surfaces.

15. The apparatus of claims 14, wherein the quadrilateral is a parallelogram.

16. The apparatus of claim 11, wherein the bias member allows the protector to move relative to the penetrator so that the penetrator penetrates the septum and extends into the tissue site to the controlled depth when the apparatus is in use and to move back after use.

17. The apparatus of claim 11, wherein the tissue site comprises a cranium.

18. The apparatus of claims 11, wherein the penetrator comprises a hollow shaft, an aperture and a tip having a quadrilateral cross-section, where the quadrilateral includes two short sides and two long sides disposed in an alternating configuration so that the short sides and longs sides are opposed and where the short sides include cutting surfaces and long sides are non-cutting surfaces.

19. The apparatus of claims 18, wherein the quadrilateral is a parallelogram.

20. An apparatus comprising:
  a. a tissue penetrator disposed in a distal portion of the apparatus;
  b. a solenoid for controlling penetrator penetration speed and depth;
  c. a motor adapted to rotate the solenoid and the penetrator,
  d. a torque sensor adapted to sensor changes in a motor torque,
  e. a power supply and associated circuitry for supplying electrical power to the solenoid;
  f. a switch for starting and stopping the solenoid;
  g. a housing surrounding the penetrator, the solenoid and the power supply; and
  h. a disposable, biased retractable protector having a septum at its distal end and a bias member, where the protector is detachably connected to a distal end of the apparatus and protects a tip of the penetrator, and where the electrical power supplied to the solenoid allows the apparatus to penetrate a tissue site including bone at a controlled rate and to a controlled depth, and where the electrical power supplied to the motor and the circuitry controls a motor speed and a motor direction, and where the electrical power supplied to the torque sensor and the circuitry turns the motor off when a change in torque evidences a transition from bone to soft tissue.

21. The apparatus of claim 20, wherein the bias member allows the protector to move relative to the penetrator so that the penetrator penetrates the septum and extends into the tissue site to the controlled depth when the apparatus is in use and to move back after use.

22. The apparatus of claim 20, wherein the tissue site comprises a cranium.

23. The apparatus of claims 20, wherein the penetrator comprises a hollow shaft, an aperture and a tip having a quadrilateral cross-section, where the quadrilateral includes two short sides and two long sides disposed in an alternating configuration so that the short sides and longs sides are opposed and where the short sides include cutting surfaces and long sides are non-cutting surfaces.

24. The apparatus of claims 23, wherein the quadrilateral is a parallelogram.

* * * * *